(12) United States Patent
Wong et al.

(10) Patent No.: US 10,966,803 B2
(45) Date of Patent: Apr. 6, 2021

(54) INTRAORAL 3D SCANNER WITH FLUID SEGMENTATION

(71) Applicant: Carestream Dental Technology Topco Limited, London (GB)

(72) Inventors: Victor C. Wong, Pittsford, NY (US); Chuanmao Fan, Rochester, NY (US); Yiyi Guan, Rochester, NY (US); Jean-Marc Inglese, Chessy-Beaubourg (FR); Edward R. Shellard, Atlanta, GA (US)

( * ) Notice: Subject to any disclaimer, the term of this patent is extended or adjusted under 35 U.S.C. 154(b) by 0 days.

(21) Appl. No.: 16/306,523

(22) PCT Filed: May 31, 2016

(86) PCT No.: PCT/US2016/034986
§ 371 (c)(1),
(2) Date: Nov. 30, 2018

(87) PCT Pub. No.: WO2017/209729
PCT Pub. Date: Dec. 7, 2017

(65) Prior Publication Data
US 2019/0133725 A1 May 9, 2019

(51) Int. Cl.
*A61C 9/00* (2006.01)
*G01B 9/02* (2006.01)
(Continued)

(52) U.S. Cl.
CPC .............. *A61C 9/0086* (2013.01); *A61B 1/24* (2013.01); *A61B 5/0066* (2013.01);
(Continued)

(58) Field of Classification Search
CPC .............. A61C 9/0053; G01B 9/02091; G06T 2207/30036; A61B 5/0095
See application file for complete search history.

(56) References Cited

U.S. PATENT DOCUMENTS

2008/0062429 A1* 3/2008 Liang ................. A61B 1/00052
356/497
2011/0054292 A1* 3/2011 Hirson ................ A61B 5/0095
600/407

(Continued)

OTHER PUBLICATIONS

"A Voice-Coil Actuated Ultrasound Micro-Scanner for Intraoral High Resolution Impression Taking"—Thorsten Vollbom, Simon Junk, Klaus Radermacher, Stefan Heger; 2012 IEEE/RSJ International Conference on Intelligent Robots and Systems; Oct. 7-12, 2012. Vilamoura, Algarve, Portugal.*

(Continued)

*Primary Examiner* — Mainul Hasan (57) ABSTRACT

A method for imaging a tooth surface, the method executed at least in part on a computer, directs an excitation signal toward the tooth from a scan head and obtains a depth-resolved response signal emanating from the tooth, wherein the response signal encodes tooth surface structure information. Liquid and tooth surfaces are segmented from the depth-resolved response signal. The tooth surface structure information is adjusted based on the segmented liquid. A 3D image of the tooth is reconstructed according to the depth-resolved response signal and the adjusted tooth surface structure information. The 3D image content is displayed, stored, or transmitted.

14 Claims, 9 Drawing Sheets

(51) Int. Cl.
*G01B 11/24* (2006.01)
*G01B 17/06* (2006.01)
*A61B 1/24* (2006.01)
*A61B 5/00* (2006.01)
*G06T 7/12* (2017.01)
*G06T 7/50* (2017.01)

(52) U.S. Cl.
CPC .......... *A61B 5/0095* (2013.01); *A61C 9/0053* (2013.01); *G01B 9/02083* (2013.01); *G01B 9/02091* (2013.01); *G01B 11/24* (2013.01); *G01B 17/06* (2013.01); *G06T 7/12* (2017.01); *G06T 7/50* (2017.01); *G06T 2207/30036* (2013.01)

(56) References Cited

U.S. PATENT DOCUMENTS

| | | | | |
|---|---|---|---|---|
| 2011/0098572 | A1* | 4/2011 | Chen | A61B 5/0066 600/463 |
| 2012/0092461 | A1* | 4/2012 | Fisker | A61B 5/0068 348/46 |
| 2013/0190591 | A1* | 7/2013 | Hirson | A61B 8/4444 600/407 |
| 2013/0190595 | A1* | 7/2013 | Oraevsky | A61B 8/4416 600/407 |
| 2015/0164335 | A1* | 6/2015 | Van Der Poel | A61B 5/0088 433/29 |
| 2015/0297329 | A1* | 10/2015 | Babayoff | H01L 27/14868 433/29 |
| 2016/0004811 | A1* | 1/2016 | Somasundaram | G06T 7/11 703/11 |
| 2016/0338803 | A1* | 11/2016 | Pesach | A61C 19/04 |
| 2019/0046276 | A1* | 2/2019 | Inglese | G06T 19/006 |

OTHER PUBLICATIONS

"A Voice-Coil Actuated Ultrasound Micro-Scanner for Intraoral High Resolution Impression Taking"—Thorsten Vollbom. Simon Junk, Klaus Radermacher, Stefan Heger; 2012 IEEE/RSJ International Conference on Intelligent Robots and Systems; Oct. 7-12, 2012. Vilamoura, Algarve, Portugal. (Year: 2012).*

"A 3-D Reconstruction System for the Human Jaw Using a Sequence of Optical Images"—Sameh M. Yamany, Aly A. Farag, David Tasman, and Allan G. Farman, IEEE Transactions on Medical Imaging, vol. 19, No. 5, May 2000 (Year: 2000).*

"Appearance-based approach for complete human jaw shape reconstruction"—Shireen Y. Elhabian, Aly A. Farag; The Institution of Engineering and Technology, IET Comput. Vis., 2014, vol. 8, Iss. 5, pp. 404-418, doi: 10.1049/iet-cvi.2013.0107 (Year: 2014).*

* cited by examiner

INTRAORAL 3D SCANNER WITH FLUID SEGMENTATION

TECHNICAL FIELD

The disclosure relates generally to the field of diagnostic imaging and more particularly to an apparatus and method for intraoral scanning. More specifically, the disclosure relates to scanning apparatus and methods for generating a 3D surface contour image with compensation for effects of saliva and other bodily fluid.

BACKGROUND

Structured light imaging has been used effectively for surface contour imaging of solid, highly opaque objects and has been used for imaging the surface contours for various portions of the human body and for obtaining detailed data about skin structure. In structured light imaging, a pattern of lines or other features is projected toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of structured light projection imaging, used in order to complete the contour mapping of the surface and to increase overall resolution in the contour image.

Surface contour information can be particularly useful for assessment of tooth condition and is helpful for various types of dental procedures, such as for restorative dentistry. A number of techniques have been developed for obtaining surface contour information from various types of objects in medical, industrial, and other applications. Optical 3-dimensional (3D) measurement methods provide shape and depth information using light directed onto a surface in various ways. Among types of imaging methods used for contour imaging are those that generate a series of light patterns and use focus or triangulation to detect changes in surface shape over the illuminated area.

Figure 1:
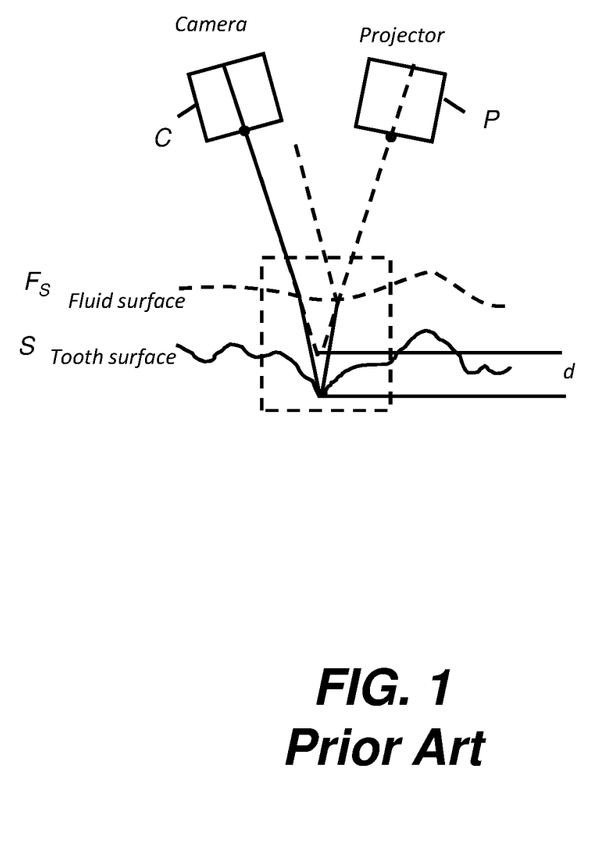
FIG. 1 is a simplified schematic diagram that shows some of the effects of light refraction through intraoral fluid.

Accurate characterization of the surface contour for teeth and other intraoral structures can be compromised due to the effects of fluids. Water, saliva, blood, and other fluids that can collect on and around the teeth can cause difficulties for reflective imaging systems. FIG. 1 shows the effect of light refraction in the presence of fluid. Light projected from a projector P will be refracted by a fluid F and partially reflected at the air-fluid interface, surface $F_S$. Thus, only a portion of the projected light impinges onto the tooth surface S. Similarly the backscattered light from the tooth surface S is again refracted at the fluid-air interface and captured by the camera C at another angle. Back-ray tracing of the projection beam and captured light beam locates an intersection point which is shifted toward the imaging system, causing image distortion. In FIG. 1, a dimension d shows the shift distance of reconstructed 3D data, appearing to be a real point on the tooth surface.

In addition to dimensional inaccuracy, reflection from the fluid can produce shining spots on images, saturated due to high reflection levels. The corresponding points cannot be used for point cloud reconstruction.

Thus, there is a need for methods and apparatus that surmount these problems and provide accurate contour imaging data for intraoral surface characterization.

SUMMARY

An object of the present disclosure is to address the need for accurate characterization of intraoral surfaces. Embodiments of the present disclosure employ techniques that provide image data without the negative effects noted previously for reflective imaging systems.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a method for imaging a tooth surface, the method executed at least in part on a computer, comprising:
   directing an excitation signal toward the tooth from a scan head;
   obtaining a depth-resolved response signal emanating from the tooth, wherein the response signal encodes tooth surface structure information;
   segmenting liquid and tooth surface from the depth-resolved response signal;
   adjusting the tooth surface structure information based on the segmented liquid;
   reconstructing a 3D image of the tooth according to the depth-resolved response signal and the adjusted tooth surface structure information;
   and
   displaying, storing, or transmitting the 3D image content.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry. The term "subject" refers to the tooth or other portion of a patient that is being imaged and, in optical terms, can be considered equivalent to the "object" of the corresponding imaging system.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2D digital image from reflected visible or NIR (near-infrared) light, such as structured light that is reflected from the surface of teeth and supporting structures.

Exemplary method and/or apparatus embodiments of the present disclosure provide a depth-resolved volume imaging for obtaining signals that characterize the surfaces of teeth, gum tissue, and other intraoral features where saliva, blood, or other fluids may be present. Depth-resolved imaging techniques are capable of mapping surfaces as well as subsurface structures up to a certain depth. Using certain exemplary method and/or apparatus embodiments of the present disclosure can provide the capability to identify fluid within a sample, such as saliva on and near tooth surfaces, and to compensate for fluid presence and reduce or eliminate distortion that could otherwise corrupt surface reconstruction.

Descriptions of the present invention will be given in terms of an optical coherence tomography imaging system. The invention can also be implemented using photo-acoustic or ultrasound imaging systems. For more detailed information on photo-acoustic and ultrasound imaging, reference is made to Chapter 7 "Handheld Probe-Based Dual Mode Ultrasound/Photoacoustics for Biomedical Imaging" by Mithun Kuniyil, Ajith Singh, Wiendelt Steenbergen, and Srirang Manohar, in *Frontiers in Biophotonics for Translational Medicine*", pp. 209-247. Reference is also made to an article by Minghua Xu and Lihong V. Wang, entitled "Photoacoustic imaging in biomedicine", *Review of Scientific Instruments* 77, (2006) pp. 041101-1 to -21.

Imaging Apparatus

Figure 2:
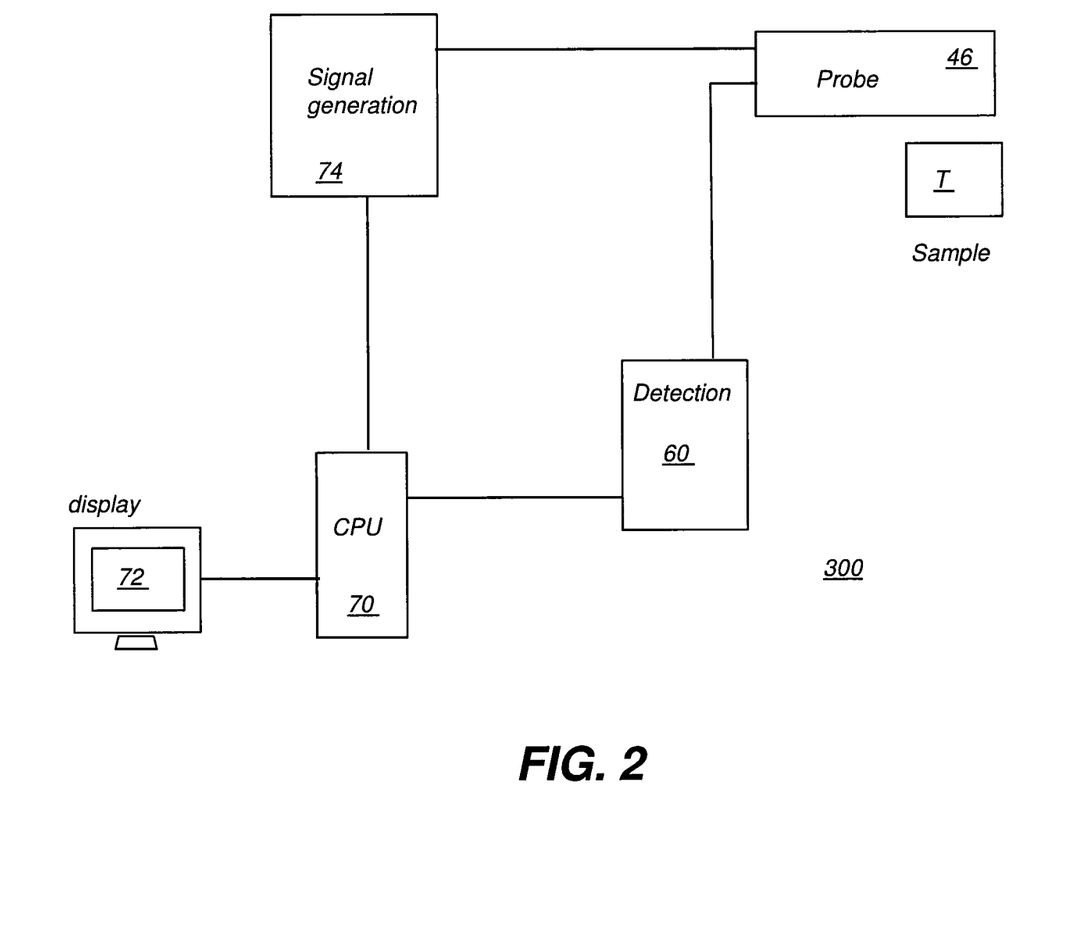
FIG. 2 shows a simplified schematic view of a depth-resolved imaging apparatus for intraoral imaging.

FIG. 2 shows a simplified schematic view of a depth-resolved imaging apparatus 300 for intraoral imaging. Under control of a central processing unit, CPU 70, and signal generation logic 74 and associated support circuitry, a probe 46 directs an excitation signal into the tooth or other intraoral feature, shown as a sample T in FIG. 2 and subsequent figures. Probe 46 can be hand-held or fixed in place inside the mouth. Probe 46 obtains a depth-resolved response signal, such as reflection and scattered signal, emanating from the tooth, wherein the response signal encodes structure information for the sampled tissue. The response signal goes to a detector 60, which provides circuitry and supporting logic for extracting and using the encoded information. CPU 70 then performs reconstruction of a 3D or volume image of the tooth surface or surface of a related feature according to the depth-resolved response signal. CPU 70 also performs segmentation processing for identifying any fluid collected on or near the sample T and to remove this fluid from the 3D surface computation. A display 72 then allows rendering of the 3D surface image content, such as showing individual slices of the reconstructed volume image. Storage and transmittal of the computed surface data or of an image showing all or only a portion of the surface data can also be performed as needed.

Following the basic model of FIG. 2, various types of signal generation logic 74 can be used to provide different types of excitation signal through probe 46. Among the excitation signal types that can be used are the following:
  (i) OCT (optical coherence tomography), using a broadband light signal for time-domain, spectral, or swept-source imaging, as described in more detail subsequently;
  (ii) ultrasound imaging, using an acoustic signal;
  (iii) pulsed or modulated laser excitation, used for photoacoustics imaging.

Depending on the type of excitation and response signals, accordingly, detection circuitry 60 processes light signal for OCT or acoustic signal for ultrasound and photo-acoustic imaging.

Figure 3:
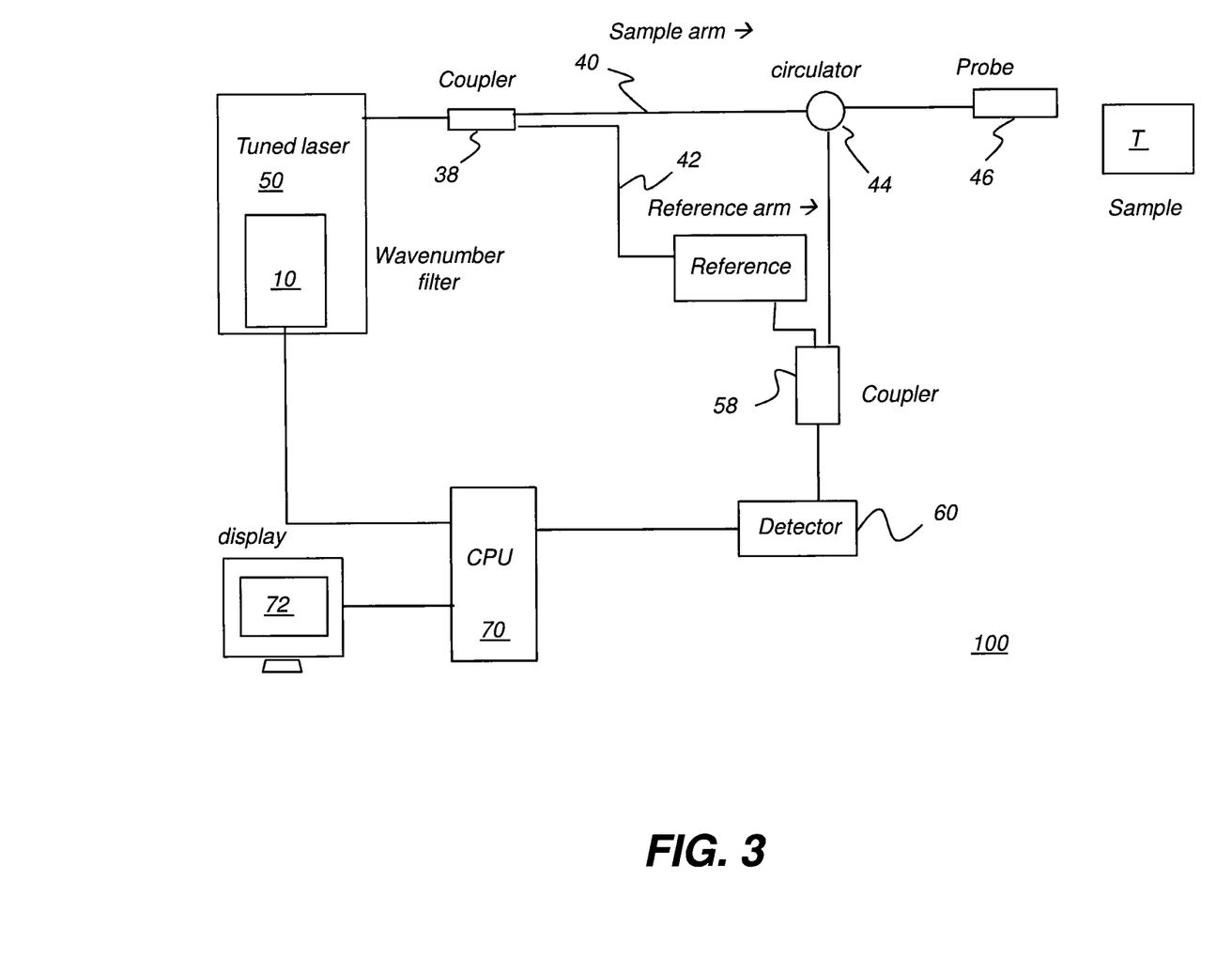
FIGS. 3 and 4 each show a swept-source OCT (SS-OCT) apparatus using a programmable filter according to an embodiment of the present disclosure.
Figure 4:
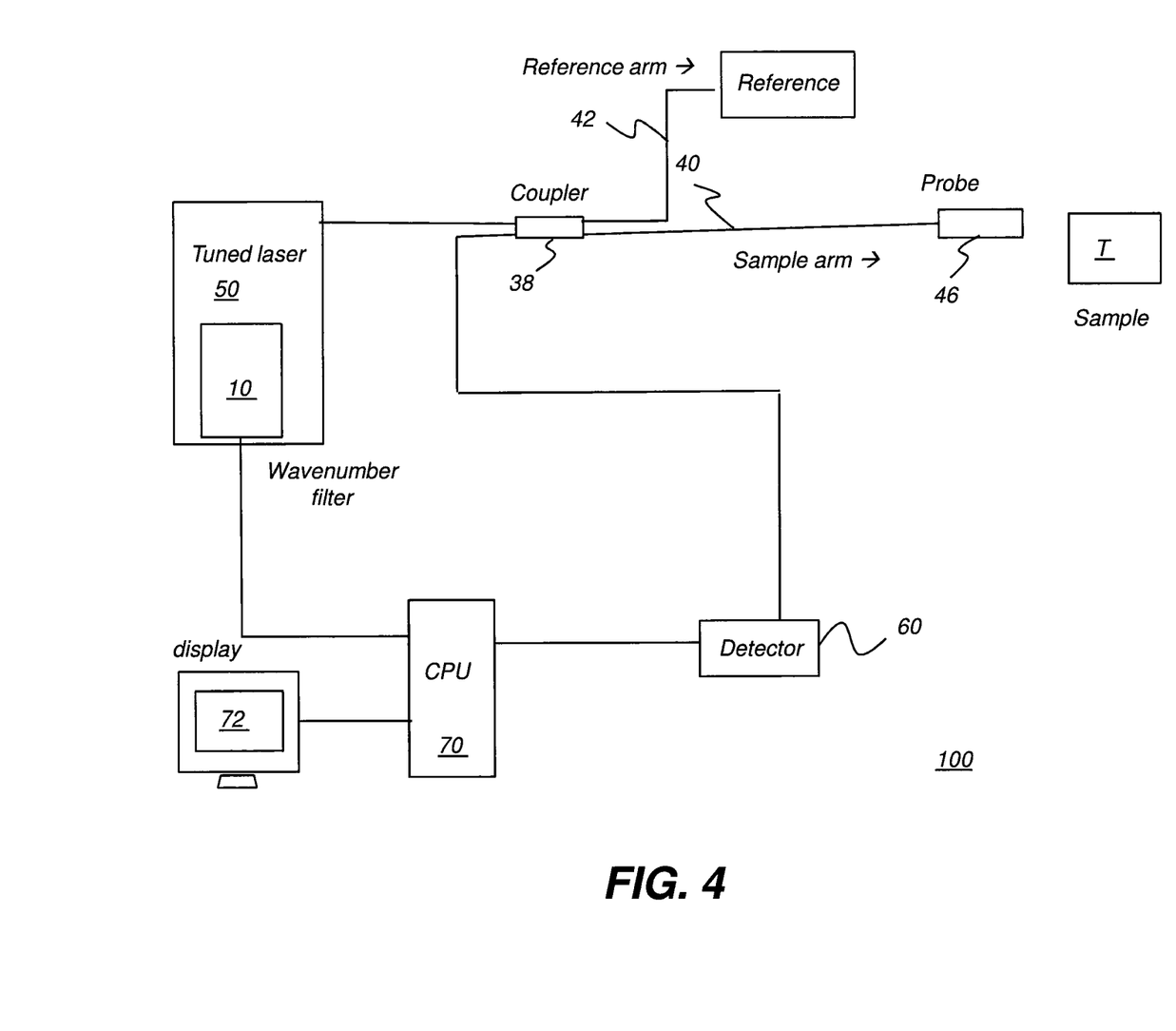

The simplified schematic diagrams of FIGS. 3 and 4 each show a swept-source OCT (SS-OCT) apparatus 100 using a programmable filter 10 according to an embodiment of the present disclosure. In each case, programmable filter 10 is used as part of a tuned laser 50 that provides an illumination source. For intraoral OCT, for example, laser 50 can be tunable over a range of frequencies (wave-numbers k) corresponding to wavelengths between about 400 and 1600 nm. According to an embodiment of the present disclosure, a tunable range of 35 nm bandwidth centered about 830 nm is used for intraoral OCT.

In the FIG. 3 embodiment, a Mach-Zehnder interferometer system for OCT scanning is shown. FIG. 4 shows components for an alternate Michelson interferometer system. For these embodiments, programmable filter 10 provides part of the laser cavity to generate a tuned laser 50 output. The variable laser 50 output goes through a coupler 38 and to a sample arm 40 and a reference arm 42. In FIG. 3, the sample arm 40 signal goes through a circulator 44 and to a probe 46 for measurement of a sample T. The sampled depth-resolved signal is directed back through circulator 44 (FIG. 3) and to a detector 60 through a coupler 58. In FIG.

4, the signal goes directly to sample arm 40 and reference arm 42; the sampled signal is directed back through coupler 38 and to detector 60. The detector 60 may use a pair of balanced photodetectors configured to cancel common mode noise. A control logic processor (control processing unit CPU) 70 is in signal communication with tuned laser 50 and its programmable filter 10 and with detector 60 and obtains and processes the output from detector 60. CPU 70 is also in signal communication with display 72 for command entry and for OCT results display, such as rendering of the 3D image content from various angles and sections or slices.

Figure 5:
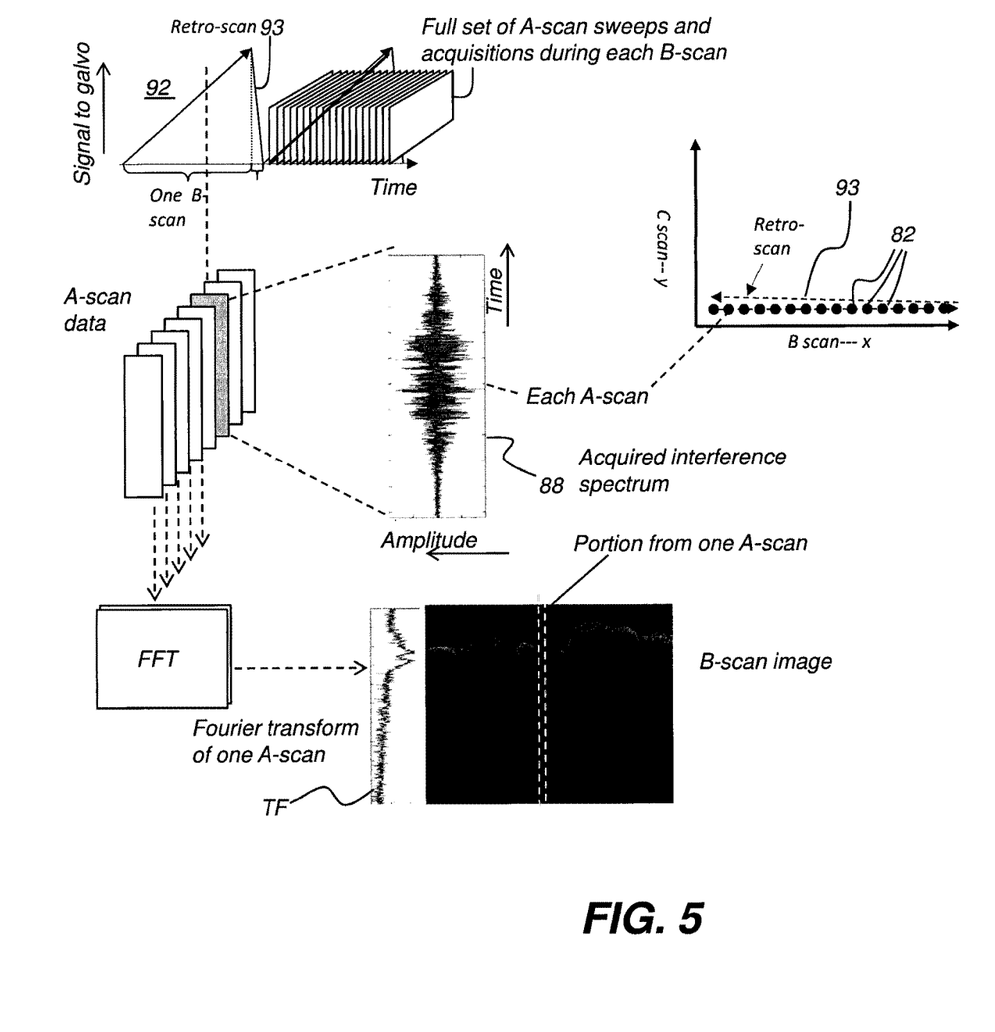
FIG. 5 is a schematic diagram that shows data acquired during an OCT scan.

The schematic diagram of FIG. 5 shows a scan sequence that can be used for forming tomographic images of an intraoral feature using the OCT apparatus of the present disclosure. The sequence shown in FIG. 5 summarizes how a single B-scan image is generated. A raster scanner scans the selected light sequence as illumination over sample T, point by point. A periodic drive signal 92 as shown in FIG. 5 is used to drive the raster scanner mirrors to control a lateral scan or B-scan that extends across each row of the sample, shown as discrete points 82 extending in the horizontal direction. At each of a plurality of points 82 along a line or row of the B-scan, an A-scan or depth scan, acquiring data in the z-axis direction, is generated using successive portions of the selected wavelength band. FIG. 5 shows drive signal 92 for generating a straightforward ascending sequence using the raster scanner, with corresponding tuning of the laser through the wavelength band. The retro-scan signal 93; part of drive signal 92, simply restores the scan mirror back to its starting position for the next line; no data is obtained during retro-scan signal 93.

It should be noted that the B-scan drive signal 92 drives the actuable scanning mechanics, such as a galvo or a microelectro-mechanical mirror, for the raster scanner of the OCT probe 46 (FIG. 3, 4). At each incremental scanner position, each point 82 along the row of the B-scan, an A-scan is obtained as a type of 1D data, providing depth-resolved data along a single line that extends into the tooth. To acquire the A-scan data with spectral OCT, a tuned laser or other programmable light source sweeps through the spectral sequence. Thus, in an embodiment in which a programmable filter causes the light source to sweep through a 30 nm range of wavelengths, this sequence for generating illumination is carried out at each point 82 along the B-scan path. As FIG. 5 shows, the set of A-scan acquisitions executes at each point 82, that is, at each position of the scanning mirror. By way of example, there can be 2048 measurements for generating the A-scan at each position 82.

FIG. 5 schematically shows the information acquired during each A-scan. An interference signal 88, shown with DC signal content removed, is acquired over the time interval for each point 82, wherein the signal is a function of the time interval required for the sweep (which has a one-to-one correspondence to the wavelength of the swept source), with the signal that is acquired indicative of the spectral interference fringes generated by combining the light from reference and feedback (or sample) arms of the interferometer (FIGS. 3, 4). The Fourier transform generates a transform TF for each A-scan. One transform signal corresponding to an A-scan is shown by way of example in FIG. 5.

From the above description, it can be appreciated that a significant amount of data is acquired over a single B-scan sequence. In order to process this data efficiently, a Fast-Fourier Transform (FFT) is used, transforming the spectral-based signal data to corresponding spatial-based data from which image content can more readily be generated.

In Fourier domain OCT, the A scan corresponds to one line of spectrum acquisition which generates a line of depth (z-axis) resolved OCT signal. The B scan data generates a 2D OCT image as a row R along the corresponding scanned line. Raster scanning is used to obtain multiple B-scan data by incrementing the raster scanner acquisition in the C-scan direction.

For ultrasound and for photo-acoustic imaging apparatus 300, the probe 46 transducer for signal feedback must be acoustically coupled to sample T, such as using a coupling medium. The acoustic signal that is acquired typically goes through various gain control and beam-forming components, then through signal processing for generating display data.

Image Processing

Embodiments of the present disclosure use depth-resolved imaging techniques to help counteract the effects of fluid in intraoral imaging, allowing 3D surface reconstruction without introducing distortion due to fluid content within the intraoral cavity. In order to more effectively account for and compensate for fluid within the mouth, there remain some problems to be addressed when using the 3D imaging methods described herein.

Among problems with the imaging modalities described for 3D surface imaging is the shift of image content due to the light or sound propagation in fluid. With either OCT or ultrasound methods, the retro-reflected signals from the imaged features provide information resolvable to different depth layers, depending on the relative time of flight of light or sound. Thus the round trip propagation path length of light or sound within the fluid can cause some amount of distortion due to differences between propagation speeds of light or sound in fluid and in air.

OCT can introduce a position shift due to the refractive index difference between the surrounding fluid medium and air. The shift is $2\Delta nd$, wherein $\Delta n$ is the difference in refractive index between fluid and air, distance d is the thickness of fluid. The factor 2 is introduced due to the round trip propagation of light through distance d.

Figure 6:
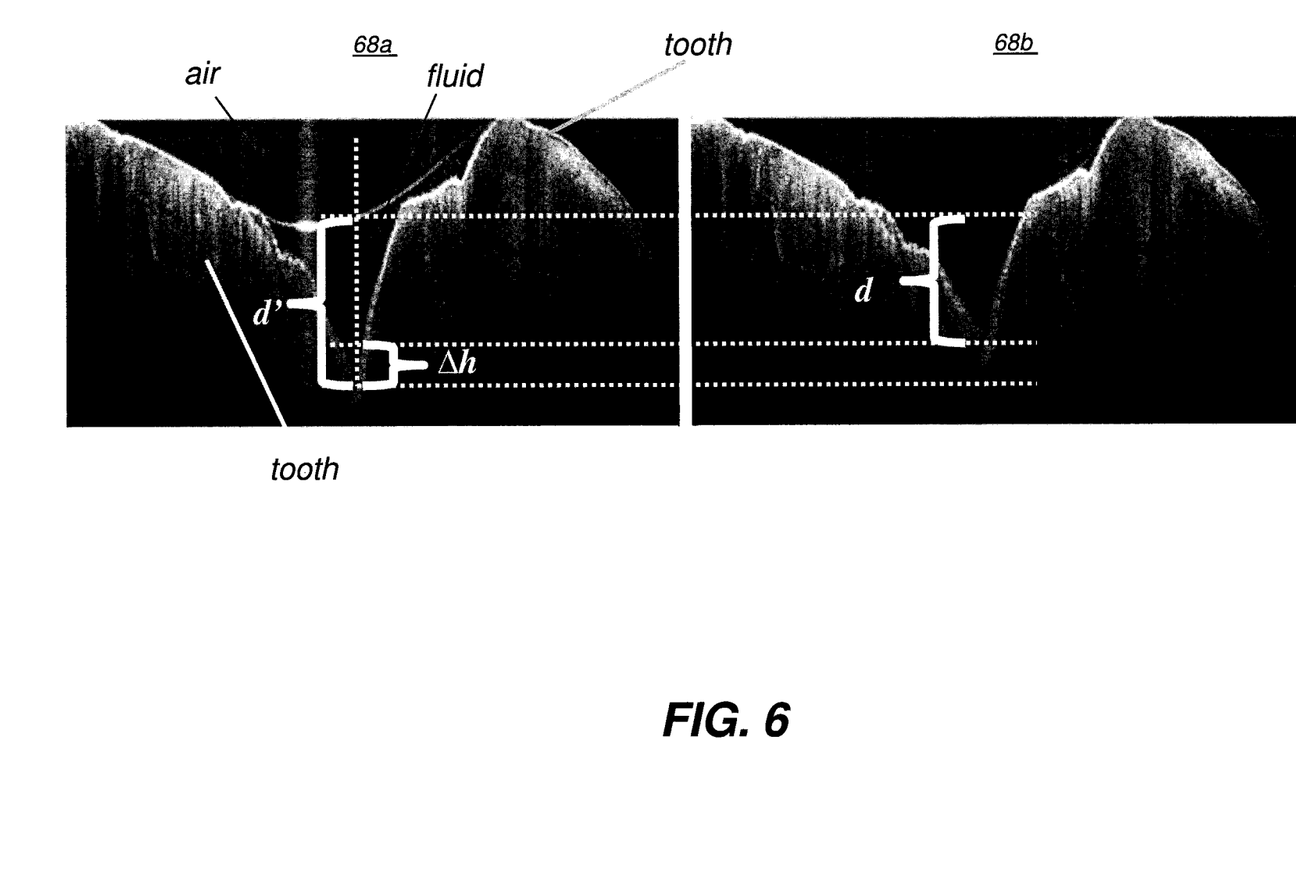
FIG. 6 shows an OCT B-scan for two teeth, with and without fluid content.

The example of FIG. 6 shows an OCT B-scan for two teeth, a first OCT scan 68a with fluid, shown side-by-side with the corresponding scan 68b without fluid content. As is shown in the example of FIG. 6, for the apparent height difference $\Delta h=\Delta n2d$ in the scan 68a, distance d' is measured from surface point of the fluid to tooth surface point. The actual position of the tooth beneath the fluid, however, is $d'/(1+\Delta n)$, for example (d'/1.34 for water).

Similarly, ultrasound has a shift effect caused by a change in the speed of sound in the fluid. The calculated shift is $\Delta c \times 2d$, wherein $\Delta c$ is the speed difference of sound between air and fluid.

Photoacoustics imaging relies on pulsed light energy to stimulate thermal extension of probed tissue in the sample. The excitation points used are the locations of the acoustic sources. Photoacoustics devices capture these acoustic signals and reconstruct the 3D depth resolved signal depending on the receiving time of sound signals. If the captured signal is from the same path of light, then the depth shift is $\Delta c \times d$, where $\Delta c$ is the speed difference of sound between air and fluid. Value d is the thickness of fluid.

Figure 7:
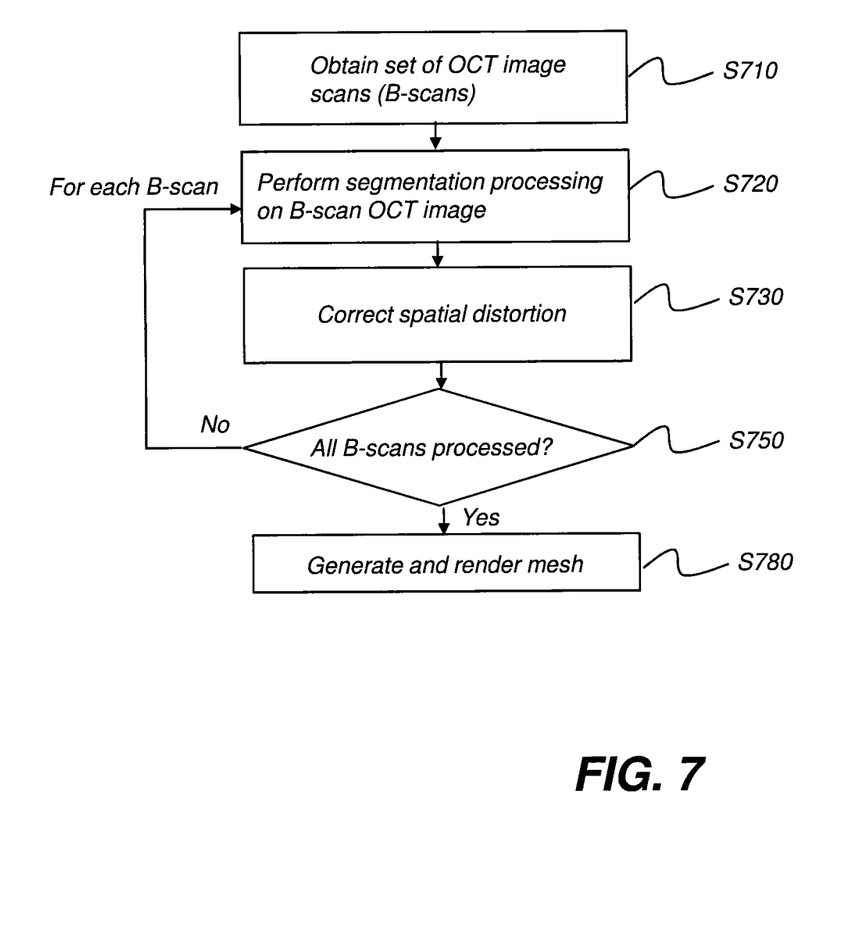
FIG. 7 is a logic flow diagram showing contour image rendering with compensation for fluid according to an embodiment of the present disclosure.
Figure 8A:
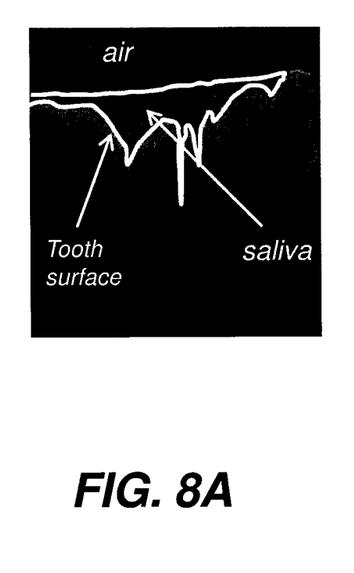
FIGS. 8A and 8B show image examples with segmentation of blood and saliva.
Figure 8B:
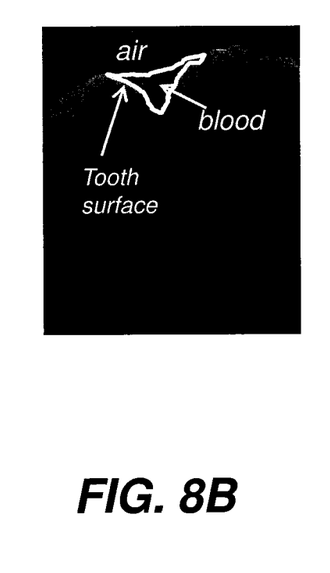

The logic flow diagram of FIG. 7 shows a processing sequence for fluid compensation using OCT imaging. In an acquisition step S710, a set of OCT image scans is obtained. Each element in the set is a B-scan, or side-view scan, such as the scans shown in FIG. 6, for example. The block of steps that follows then operates on each of the acquired B-scans. A segmentation step S720 identifies fluid and tooth surfaces from the B-scan image, by detecting multiple interfaces as shown in the schematic diagram of FIG. 1. Segmentation step S720 defines the tooth surface and the area of the B-scan image that contains intraoral fluid such as water, saliva, or blood, as shown in the example of FIGS. 8A and 8B. Then, in order to obtain more accurate characterization of the 3D surfaces, a correction step S730 corrects for spatial distortion of the tooth surface underneath the fluid due to refractive index differences between air and the intraoral fluid. Step S730 adjusts the measured depth of segmented regions in the manner discussed above, based on the thickness of the region and refractive index of the fluid within the region. For example, the refractive index of water for the OCT illumination is approximately 1.34; for blood in a 50% concentration, the refractive index is slightly higher, at about 1.36.

The thickness of the region is determined through a calibrated relationship between the coordinate system inside the OCT probe and the physical coordinates of the teeth, dependent on the optical arrangement and scanner motion inside the probe. Geometric calibration data are obtained separately by using a calibration target of a given geometry. Scanning of the target and obtaining the scanned data establishes a basis for adjusting the registration of scanned data to 3D space and compensating for errors in scanning accuracy. The calibration target can be a 2D target, imaged at one or more positions, or a 3D target.

The processing carried out in steps S720 and S730 of FIG. 7 is executed for each B-scan obtained by the OCT imaging apparatus. A decision step S750 then determines whether or not all B-scans in the set have been processed. Once processing is complete for the B-scans, the combined B-scans form a surface point cloud for the teeth. A mesh generation and rendering step S780 then generates and renders a 3D mesh from the surface point cloud. The rendered OCT surface data can be displayed, stored, or transmitted.

Various image segmentation algorithms can be used for the processing described with relation to FIG. 7, including simple direct threshold, active contour level set, watershed, supervised and unsupervised image segmentation, neural network based image segmentation, spectral embedding, k-means, and max-flow/min-cut graph based image segmentation, for example. Segmentation algorithms are well known to those skilled in image processing and can be applied to the entire 3D volume, reconstructed from the OCT data, or applied separately to each 2D frame or B-scan of the tomographic data prior to 3D volume reconstruction, as described above.

Processing for photoacoustics and ultrasound imaging is similar to that shown in FIG. 7, with appropriate changes for the signal energy that is detected.

Figure 9:
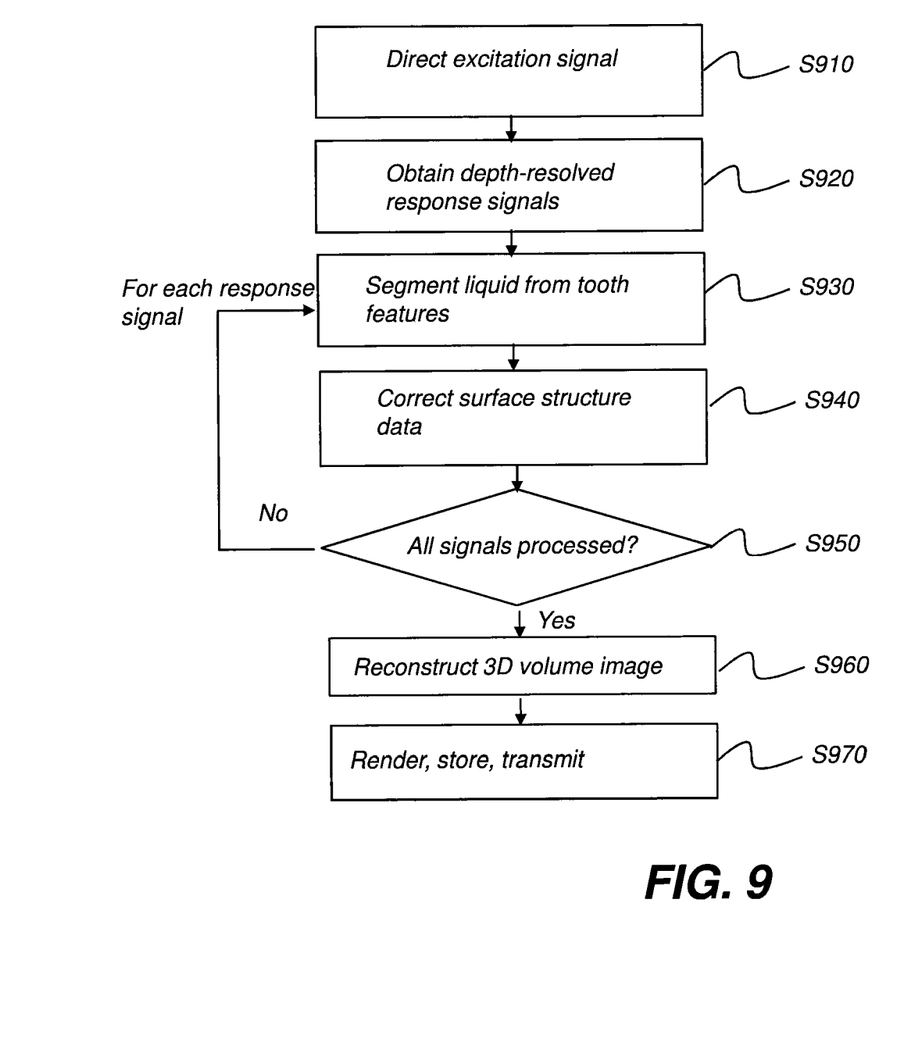
FIG. 9 is a logic flow diagram that shows a sequence that can be used for imaging a tooth surface according to an embodiment of the present disclosure.

The logic flow diagram of FIG. 9 shows a sequence that can be used for imaging a tooth surface according to an embodiment of the present disclosure. In a signal excitation step S910, an excitation signal is directed toward the subject tooth from a scan head, such as an OCT probe or a scan head that directs light for a photoacoustic imaging apparatus or sound for an ultrasound apparatus. An acquisition step S920 acquires the depth-resolved response signal that results. The depth-resolved response signal can be light or sound energy, for example, that encodes information about the structure of the tooth surface. A segmentation step S930 then segments liquid from tooth and gum features from the depth-resolved response signal. Surface structure information from the depth-resolved response signal can then be corrected using the segmentation data in an adjustment step S940. A looping step S950 determines whether or not additional depth-resolved response signals must be processed. A reconstruction step S960 then reconstructs a 3D image of the tooth according to the depth-resolved response signal and the adjusted tooth surface structure information. A rendering step S970 then renders the volume image content for display, transmission, or storage.

Consistent with an embodiment, the present invention utilizes a computer program with stored instructions that control system functions for image acquisition and image data processing, such as using the control logic processor of the present disclosure. As can be appreciated by those skilled in the image processing arts, a computer program of an embodiment of the present invention can be utilized by a suitable, general-purpose computer system, such as a personal computer or workstation that acts as an image processor (CPU), when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

Certain exemplary method and/or apparatus embodiments according to the application can provide virtual definition of the base of a dental virtual model. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

What is claimed is:

1. A method for imaging a tooth surface, the method executed at least in part on a computer, comprising:
    directing an excitation signal toward the tooth from a scan head;
    obtaining a depth-resolved response signal emanating from the tooth, wherein the response signal encodes tooth surface structure information;
    segmenting liquid and tooth surface from the depth-resolved response signal;
    adjusting the tooth surface structure information using the refractive index of the segmented liquid;
    reconstructing a 3D image of the tooth according to the depth-resolved response signal and the adjusted tooth surface structure information; and
    displaying, storing, or transmitting the 3D image content.

2. The method of claim 1 wherein the excitation signal is a broadband light signal.

3. The method of claim 1 wherein the excitation signal is a pulsed or modulated laser source.

4. The method of claim 1 wherein the excitation signal is an acoustic signal.

5. The method of claim 1 wherein the depth-resolved response signal is an acoustic signal.

6. The method of claim 1 wherein reconstructing the 3D image of the tooth comprises generating an optical coherence tomography image.

7. The method of claim 1 wherein adjusting the tooth surface includes performing geometric calibration.

8. The method of claim 1 further comprising rendering of the reconstructed 3D image.

9. The method of claim 1 wherein the depth-resolved response signal is 1D data or a 2D or 3D image.

10. The method of claim 1 wherein the scan head is hand-held or fixed inside the mouth.

11. The method of claim 1 wherein the fluid is water, saliva, or blood.

12. A method for imaging a tooth surface, the method executed at least in part on a computer, comprising:
    directing an excitation light or acoustic signal toward the tooth from a scan head;
    obtaining an acoustic response signal from the tooth in response to the excitation light or acoustic signal, wherein the acoustic response signal encodes tooth surface structure information;
    segmenting liquid and tooth surface from the acoustic response signal;
    adjusting the tooth surface structure information based at least in part on the refractive index of the segmented liquid;
    reconstructing a 3D image of the tooth according to the acoustic response signal and the adjusted tooth surface structure information; and
    displaying, storing, or transmitting a portion of the reconstructed 3D image.

13. An apparatus for imaging a tooth surface comprising:
    a signal generator that is configured to generate an optical or acoustic signal;
    a probe that is configured to scan the generated signal to the tooth for imaging and to sense a feedback depth-resolved signal from the tooth;
    a control logic processor that is programmed with stored instructions that control the signal generator, acquire the sensed feedback signal from the tooth, generate depth-resolved data from the acquired feedback signal, segment intraoral fluid and tooth surface from the generated depth-resolved data, adjust the segmented tooth surface data using the refractive index of the intraoral fluid, and form a 3D image of the tooth surface; and
    a display in signal communication with the control logic processor.

14. The apparatus of claim 13 wherein the probe generates an optical signal and senses a feedback acoustic signal.

* * * * *